(12) United States Patent
Aboul-Hosn et al.

(10) Patent No.: US 7,090,659 B2
(45) Date of Patent: Aug. 15, 2006

(54) APPARATUS AND METHODS FOR ENTERING CAVITIES OF THE BODY

(75) Inventors: Walid N Aboul-Hosn, Sacramento, CA (US); William R Kanz, Sacramento, CA (US); Roland W Zieglier, Cameron Park, CA (US); Kelly J McCrystle, Healdsburg, CA (US); Rosalind Castor, Sacramento, CA (US); Allan deDios, Sacramento, CA (US)

(73) Assignee: A-Med Systems, Inc., W. Sacramento, CA (US)

( * ) Notice: Subject to any disclaimer, the term of this patent is extended or adjusted under 35 U.S.C. 154(b) by 0 days.

(21) Appl. No.: 10/764,664

(22) Filed: Jan. 26, 2004

(65) Prior Publication Data

US 2004/0158206 A1 Aug. 12, 2004

Related U.S. Application Data

(60) Division of application No. 09/720,016, filed on Apr. 16, 2001, now Pat. No. 6,709,418, which is a continuation-in-part of application No. 09/099,713, filed on Jun. 19, 1998, now abandoned, which is a continuation-in-part of application No. 08/891,456, filed on Jul. 11, 1997, now Pat. No. 6,123,725.

(60) Provisional application No. 60/113,727, filed on Dec. 23, 1998.

(51) Int. Cl.
*A61H 9/00* (2006.01)

(52) U.S. Cl. .......................... 604/158; 604/8; 606/194; 623/3.26; 128/898

(58) Field of Classification Search ............... 604/4.01, 604/6.01, 6.05, 6.1, 6.11, 6.13, 6.14, 6.16, 604/19, 27, 28, 39–41, 43, 44, 500, 507, 604/508–509, 96.01, 164.09, 164.11, 164.01, 604/264, 523, 533–534, 8; 422/44–46; 623/3.1, 623/3.26; 600/433–435; 606/191, 192, 606/194; 435/283.1, 284.1; 128/898
See application file for complete search history.

(56) References Cited

U.S. PATENT DOCUMENTS

| 4,129,129 A | 12/1978 | Amrine |
| 4,362,163 A | 12/1982 | Krick |
| 4,508,535 A | 4/1985 | Joh et al. |
| 4,682,978 A | 7/1987 | Martin |
| 4,955,856 A | 9/1990 | Phillips |
| 5,147,388 A | 9/1992 | Yamazaki |
| 5,630,823 A | 5/1997 | Schmitz-Rode et al. |

(Continued)

FOREIGN PATENT DOCUMENTS

WO WO 99/02204 1/1999

(Continued)

*Primary Examiner*—Henry Bennett
*Assistant Examiner*—Camtu Nguyen
(74) *Attorney, Agent, or Firm*—Ryan Kromholz & Manion, S.C.

(57) ABSTRACT

Systems and methods for providing cardiac support provide a cannula body having an inlet and an outlet. The cannula includes a preformed bend sized and configured to extend within the heart chamber between the inlet and the outlet. The cannula is inserted through a first valve into a heart chamber and through a second valve out of the heart chamber. Blood is drawn into the cannula through the inlet and discharged from the cannula through the outlet, thereby bypassing the heart chamber.

3 Claims, 13 Drawing Sheets

U.S. PATENT DOCUMENTS

| | | |
|---|---|---|
| 5,702,412 A | 12/1997 | Popov et al. |
| 5,741,234 A | 4/1998 | Aboul-Hosn |
| 5,771,888 A | 6/1998 | Keim |
| 5,817,057 A | 10/1998 | Berenstein et al. |
| 5,976,103 A | 11/1999 | Martin |
| 5,980,503 A | 11/1999 | Chin |
| 6,083,260 A | 7/2000 | Aboul-Hosn |
| 6,086,570 A | 7/2000 | Aboul-Hosn |
| 6,113,536 A | 9/2000 | Aboul-Hosn et al. |
| 6,123,725 A | 9/2000 | Aboul-Hosn |
| 6,152,704 A | 11/2000 | Aboul-Hosn et al. |
| 6,186,981 B1 | 2/2001 | Cho |
| 6,210,133 B1 | 4/2001 | Aboul-Hosn et al. |
| 6,210,397 B1 | 4/2001 | Aboul-Hosn et al. |
| 6,228,063 B1 | 5/2001 | Aboul-Hosn |
| 6,234,960 B1 | 5/2001 | Aboul-Hosn et al. |
| 6,287,319 B1 | 9/2001 | Aboul-Hosn et al. |
| 6,295,877 B1 | 10/2001 | Aboul-Hosn et al. |
| 6,395,026 B1 | 5/2002 | Aboul-Hosn et al. |
| 6,709,418 B1 | 3/2004 | Aboul-Hosn et al. |

FOREIGN PATENT DOCUMENTS

| | | |
|---|---|---|
| WO | WO 99/59652 | 11/1999 |

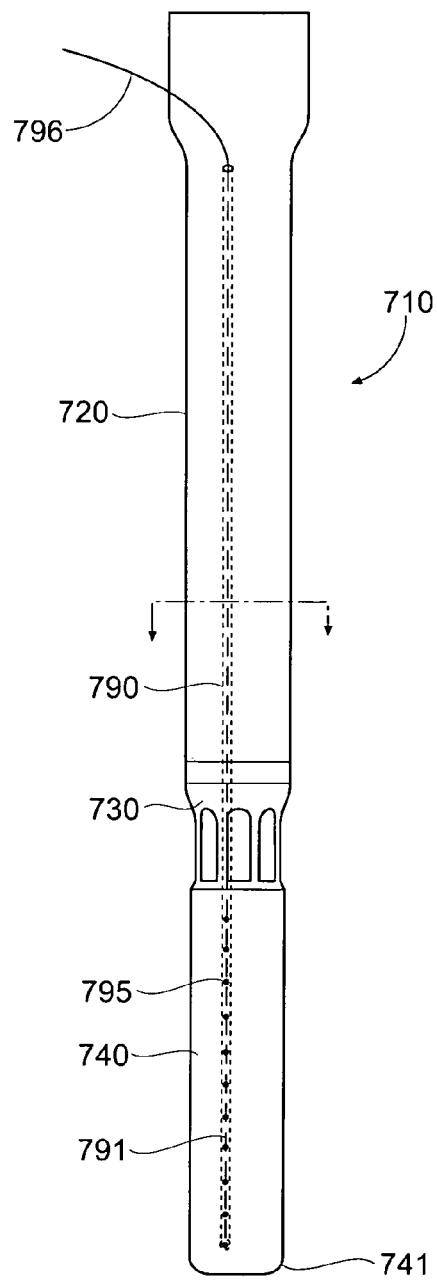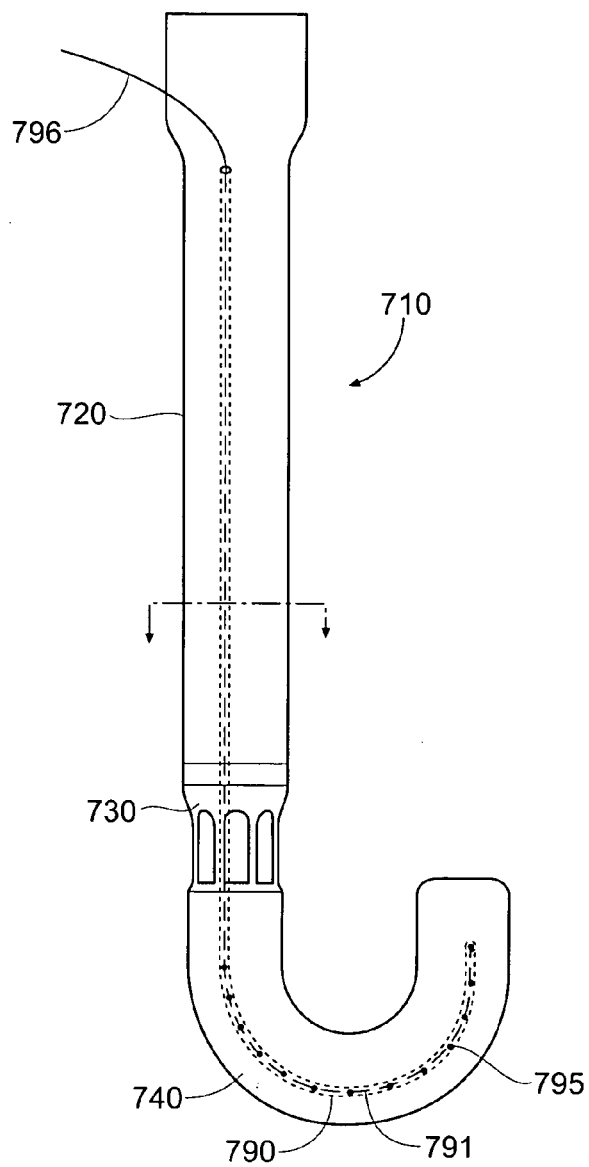
Fig. 26
Fig. 27

APPARATUS AND METHODS FOR ENTERING CAVITIES OF THE BODY

RELATED APPLICATIONS

This application is a divisional of U.S. application Ser. No. 09/720,016, filed Apr. 16, 2001 now U.S. Pat. No. 6,709,418, which is continuation-in-part of U.S. application Ser. No. 09/099,713, filed Jun. 19, 1998 (now abandoned), which claims the benefit of U.S. application Ser. No. 08/891,456, filed Jul. 11, 1997 (now U.S. Pat. No. 6,123,725) and provisional U.S. Application Ser. No. 60/113,727, filed Dec. 23, 1998.

FIELD OF THE INVENTION

The present invention is directed to related apparatus systems, equipment and methods for entering cavities of the body.

BACKGROUND OF THE INVENTION

The current trend in medicine is to perform less invasive procedures so as to minimize the trauma to the patient and shorten the recovery period. A major emphasis is to make as few incisions and as small of an incision as is possible to gain access to the interior of the patient. One area of medicine in which these techniques are being used more frequently is in heart surgery. Open heart surgery typically requires significant hospitalization and recuperation time for the open heart surgery to perform various surgical procedures such as coronary artery bypass grafting (CABG) is highly traumatic to the patient. In addition, open heart procedures require the use of cardiopulmonary bypass (CPB) which continues to represent a major assault on a host of body systems.

The CABG procedure generally involves open chest surgical techniques to patient is cut in order to spread the chest apart and provide access to the heart. During surgery the heart is stopped, and by the use of CPB blood is diverted from the lungs to an artificial oxygenator. In general, a source of arterial blood is then connected to a coronary artery downstream from the occlusion. The source of blood is often an internal artery, and the target coronary artery is typically among the anterior or posterior arteries which may be narrowed or occluded.

Multiple incisions have to be made in the arteries to accomplish the diversion of the blood. The leading cause of morbidity and disability following cardiac surgery is cerebral complications. At each incision, there is a risk of gaseous and solid micro and macro emboli, and less often perioperative cerebral hypoperfusion, which produce neurologic effects ranging from subtle neuropsychologic deficits to fatal stroke. Therefore, there is a need to minimize the number and size of incisions.

Open heart surgery is just one area of medicine, that would benefit from less invasive apparatus and procedures, others include dialysis and laparoscopic surgery just to name a couple.

Two obstacles to performing surgery is the number of incisions that must be made in various arteries, vessels, ventricles, atriums and cavity walls of the patient and the safe insertion and withdrawal of various devices and elements through those incisions.

One application for cannulas involves the augmenting or supplementation of pulmonary blood flow through the beating heart during heart surgery by use of one or more cannulas involved in the intake and return of blood into the circulatory system. The cannulas interface between the patient's circulatory system and the mechanical pumps that power the argumentation procedure.

When performing cardiac surgery cannulas are placed within the patient's blood stream and used for inflow and outflow of blood or other fluids. One such bypass circuit would be a cardiopulmonary bypass circuit (CPB), in which an outflow cannula is placed in the patient's right atrium and a return cannula is placed in the aorta. The outflow cannula can be further connected to an oxygenator, blood filter, or blood heater. Even though there are negative side effects of using on pump bypasses, doctors continue to do so because of the ease and reliability of establishing the circuit.

Though presently there is a movement away from stopped heart CPB to beating heart surgery. The movement to beating heart surgery is hampered by common bypass techniques and equipment. One such problem occurs while performing a coronary artery bypass graft (CABG) on the back side of the heart. In order to access vessels on the back side of the heart the surgeon must rotate the heart. Though rotating the heart while the heart is still beating raises new complications that were not present during stopped heart surgery. Many times rotating the beating heart leads to further complications such as a decrease in pulmonary pressure which results in a decrease in oxygen content in the patient's blood. Thus many times when a surgeon is performing a graft on the back side of the heart, the heart must be rotated and replaced many times to stabilize the patient's blood pressure.

SUMMARY OF THE INVENTION

The present invention provides cannula devices which can be inserted through an incision in a body cavity to allow ingress and egress in separate cannulas simultaneously through the incision with minimal trauma. One aspect of the present invention provides a cannula device which has at least two openings at least one of which initially is concealed or closed but which after being inserted through the wall of a cavity (for example, the aorta) can be opened to allow ingress and egress through the two openings simultaneously through the incision in the wall of the cavity. One embodiment provides a cannulation device for access to an interior body region comprises a cannula body having a distal end for insertion through an incision and including first and second interior flow paths to circulate fluid. A conduit communicates with one of the first and second flow paths and extends beyond the distal end of the cannula body to input or outflow fluid at an area of the interior body region spaced from the distal end. A port communicates with the other one of the first and second flow paths to input or outflow fluid at the distal end. A closure assembly on the cannula body operates in a first condition to close the port, thereby preventing fluid circulation within the cannula body between the first and second flow paths. The closure assembly operates in a second condition to open the port, thereby allowing fluid circulation within the cannula body between the first and second flow paths.

Another aspect of the invention provides a system for circulating blood in a heart. The system comprises a cannula body having a distal end for insertion through an incision and including first and second interior flow paths to circulate blood. A conduit communicates with one of the first and second flow paths. The conduit is sized to extend, in use, beyond the distal end of the cannula body for passage into a heart chamber, to thereby input or outflow blood from the heart chamber. The conduit includes a preformed, bent region to direct its passage from the distal end into the heart chamber. A port communicates with the other one of the first and second flow paths to input or outflow blood at the distal end.

Another aspect of the invention provides a cannula for access to an interior body region comprising a body defining a lumen having a distal region. The lumen includes a two dimensional configuration e.g., one or more bends, in the distal region to aid placement of the cannula in the interior body region.

Any aspect of the invention is usable in association with a pump, which operates, in use, to intake fluid and output fluid. Another aspect of the invention provides a method of providing cardiac support. The method provides a cannula body having an inlet and an outlet. The cannula includes a preformed bend sized and configured to extend within the heart chamber between the inlet and the outlet. The cannula is inserted through a first valve into a heart chamber in an antegrade flow direction and through a second valve out of the heart chamber in an antegrade flow direction. Blood is drawn into the cannula through the inlet upstream of the first valve and discharged from the cannula through the outlet downstream of the second valve, thereby bypassing the heart chamber. In one embodiment, the chamber is a right ventricle, the first valve is a tricuspid valve, and the second valve is a pulmonary valve.

According to yet another aspect of the invention, a method of providing cardiac support provides a cannula body having an inlet and an outlet. The cannula includes a preformed bend sized and configured to extend within the heart chamber between the inlet and the outlet. The cannula is inserted through a first valve into a heart chamber in a retrograde flow direction and through a second valve out of the heart chamber in a retrograde flow direction. Blood is drawn into the cannula through the inlet upstream of the second valve and discharged from the cannula through the outlet downstream of the first valve, thereby bypassing the heart chamber. In one embodiment, the heart chamber is a left ventricle, the first valve is an aortic valve, and the second valve is a mitral valve.

BRIEF DESCRIPTION OF THE DRAWINGS

Many objects and advantages of the present invention will be apparent to those skilled in the art when this specification is read in conjunction with the attached drawings wherein like reference numbers are applied to like elements.

FIG. 26 a side view of another cannula system capable, in use, of being inserted through the wall of a cavity, and having a distal region with resistive wire disposed within the cannula wall to bend the distal region to aid insertion of a cannula into a heart chamber; and FIG. 27 is a side view of the cannula system shown in FIG. 26 after activating the resistive wire to bend the distal region.

DETAILED DESCRIPTION OF THE PREFERRED EMBODIMENT

Figure 1:
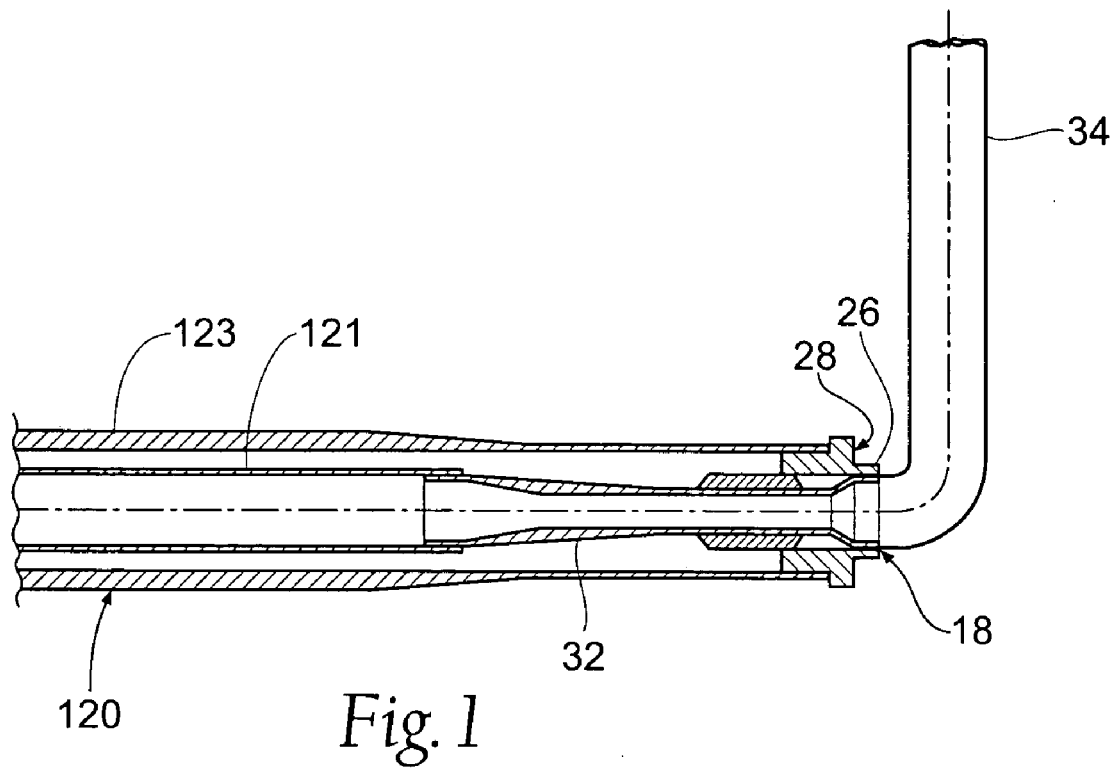
FIG. 1 is a cross-sectional view of a cannula capable, in use, of being inserted through the wall of a cavity, and having a bent distal region to direct passage into a heart chamber and a closure assembly that opens and closes fluid circulation within the cannula, the closure assembly being shown in the closed condition.

In a first embodiment of the present invention, a cannula system 120 (FIG. 1) utilizes a concentric double-wall cannula having an outer cannula 123 forming an annular space 24 around a portion of an inner cannula 121. The cannula system 120 can be a conduit for naturally flowing, fluid, pressurized fluid, or can be connected to a miniaturized reverse flow pump 124 shown diagrammatically in FIG. 2. The concentric double cannula system 120 is inserted into a body cavity 22, such as in the wall of the aorta, abdomen, or any body cavity through a single incision such that the inner cannula 121 provides intake for the fluid entering the reverse flow pump 124 and the outflow of the reverse flow pump feeds into the outer cannula 123, or vice versa.

Figure 2:
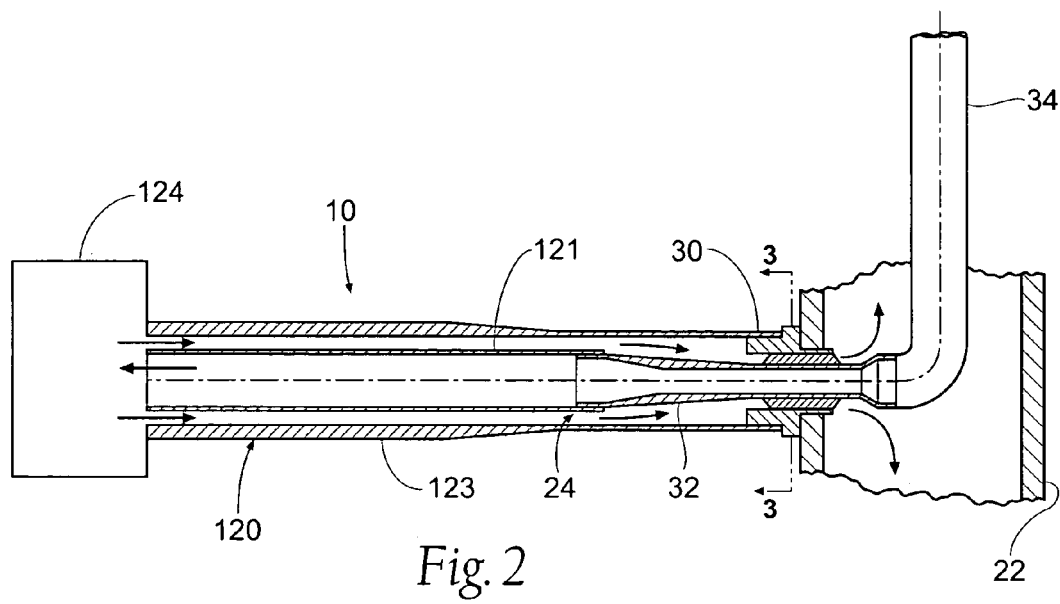
FIG. 2 is a cross-sectional view of the cannula of FIG. 1, with the closure assembly shown in the opened condition and with a pump attached.

Referring to FIG. 1, before the double cannula system 120 with flexible inlet conduit 34 attached thereto is inserted through the incision in the body cavity 22, the inner cannula 121 is moved proximally within the outer cannula 123 so that a seal exists as shown generally at 18 between the distal portion 26 of the flange connector 28 and the outer diameter of the inlet. In this way, the system is inserted through the incision with a single outside diameter and a concealed or closed flow outlet but which provides maximum fluid flow during operation. As one of ordinary skill will appreciate, the outside diameter depends on the type of body cavity to be entered and the age and size of the patient. For example, the diameter might be as large as 60 French for abdominal access, 28 French or less for the aorta, 44 French for the right or left atrium, 12 French for a baby, or even 8 French for pumping blood in a 300 pound male's coronary artery. Once the system is fully inserted into the incision, the inner cannula 121 is moved distally within the outer cannula 123 to open the flow outlet as shown in FIG. 2. For easy withdrawal, the inner cannula is retracted to close the outlet and the cannula system is withdrawn through the incision. A preferred reverse flow pump 124 is disclosed in copending U.S. application Ser. No. 08/933,566 filed Sep. 19, 1997, the disclosure of which is incorporated herein by reference. While FIG. 2 illustrates a preferred pump configuration, it is apparent any suitable pump design or configuration can be used in this invention. For example, the drive motor can be integral with pump 124, as shown diagrammatically or can be a remote motor (not shown) connected to the pump by a sheathed flexible drive cable (not shown). While the concentric double cannula system 120 is particularly useful with the reverse flow pump, other commercially available pumps can be used with such a cannula system. For example, other pumps which can be adapted for use in this invention are disclosed in U.S. Pat. Nos. 4,625,712, 5,376,114 and 5,695,471, the disclosures of which are incorporated herein by reference.

Figure 5:
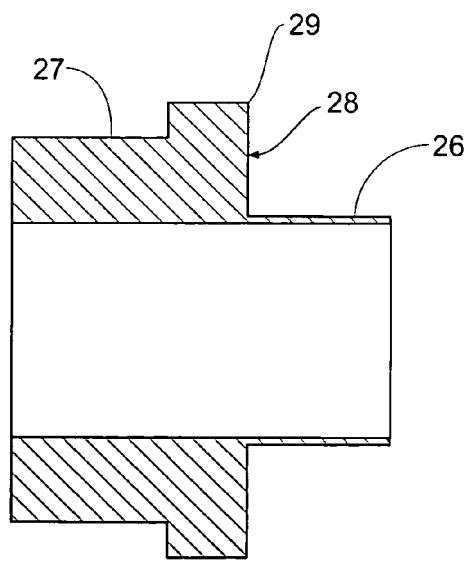
FIG. 5 is an enlarged cross-sectional view of a flange adapter that the cannula shown in FIG. 1 includes.

The pump and cannula system 120 of the first embodiment can best be understood by reference to the illustration in FIG. 2, which shows the pump 124 diagrammatically and double cannula system 120 in place in the body cavity 22 through a single incision in the wall of body cavity 22 as illustrated. The double cannula system 120 is inserted into the incision such that a cylindrical distal portion 26 of a flange connector 28 (FIG. 5) forms a seal with the wall of the body cavity 22 at the incision. The proximal portion 27 of flange connector 28 receives the distal portion 30 of the outer cannula 123. As will be recognized by one of ordinary skill in the art, it is within the scope of the invention for flange connector 28 to be an integral portion of outer cannula 123 as shown in some of the embodiments discussed below.

Flange 29 of flange connector 28 abuts the outer wall of body cavity 22 to improve the seal between the flange connector 28 and the body cavity 22 and for optional purse string anastomosis to prevent fluid loss. In this regard, an inflatable annular balloon (not shown) can be provided around the distal portion 26 of flange connector 28 which can be inflated after the cannula system 120 has been inserted through the incision to form an improved seal along the inner surface of the body cavity. A typical procedure would involve incision, cannulation, opening the concealed port, hemostasis control at the proximal end, and attachment of the pump.

Figure 3:
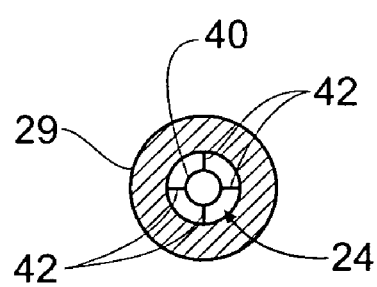
FIG. 3 is a cross-sectional view of the cannula as taken along line 3—3 of FIG. 2.
Figure 4:
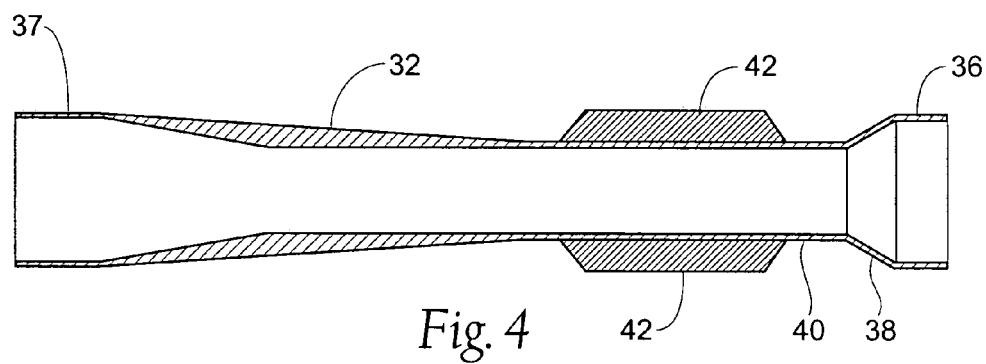
FIG. 4 is an enlarged cross-sectional view of the inner cannula of FIG. 1.
Figure 6:
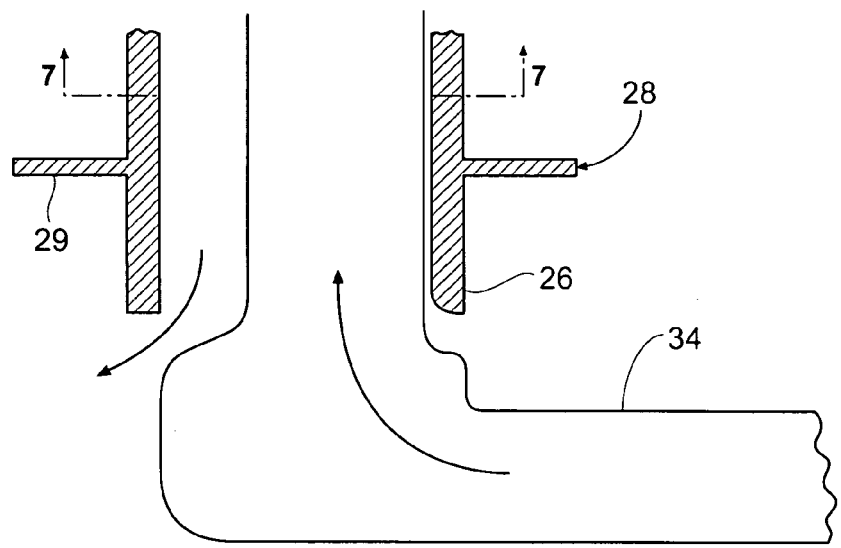
FIGS. 6 and 7 are enlarged cross-sectional views of another embodiment of a cannula capable, in use, of being inserted through the wall of a cavity, and having a bent distal region and a closure assembly that opens and closes fluid circulation within the cannula.
Figure 7:
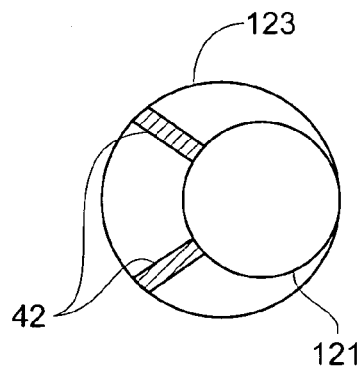

The annular space 24 between outer cannula 123 and inner cannula 121 allows outflow of fluid from pump 124. The inner cannula 121 has an adapter portion 32 (FIG. 4) which can be integral with or attached to the inner cannula 121 and flexible inlet conduit 34, which inlet conduit extends along a portion of the length of the body cavity 22 as shown in FIG. 2. The flexible inlet conduit 34 is illustrated as a right angled conduit and the flange connector 28 is illustrated as being, inserted perpendicular to the body cavity but it is within the scope of the invention for the flange connector to enter the body cavity at an angle less than 90 degrees and for the flexible inlet conduit to have a more gradual bend rather than a 90 decree bend. The adapter portion 32, best seen in FIG. 4, has an enlarged cylindrical distal end 36 mating the inlet conduit 34 to the adapter portion. The cylindrical distal end 36 tapers down internally and externally along section 38 to generally cylindrical section 40. The internal reduction in section 38 reduces the inner diameter of the inlet conduit 34 down to the inner diameter of the generally cylindrical section 40 to funnel the fluid flow into inner cannula 121. The adapter portion 32 has a constant inner diameter along substantially all of the length of generally cylindrical section 40 which then flares open to a larger inner diameter at the proximal end 37 of the adapter 32 to mate with the larger, relatively speaking, inner diameter of the inner cannula 121. Section 40 of the adapter 32 is described as being generally cylindrical rather than strictly cylindrical because the outside diameter of section 40 increases Gradually from about the vanes 42 to its proximal end 37. Vanes 42 act to center the adapter portion 32 and thus inner cannula 121 in the flange connector 28 and outer cannula 123 while allowing blood to pass from annular space 24 into aorta 22 as shown in FIGS. 2 and 3. Each of the elements have been shown and described as being generally cylindrical but it is within the scope of the invention that those elements be elliptical or other shapes. The double cannula for intake and output can have any desired configuration, such as side-by-side cannulas, multi-cannula tubing, axially offset cannulas (FIGS. 6 and 7), and others which will be apparent to one skilled in the art.

Figure 10:
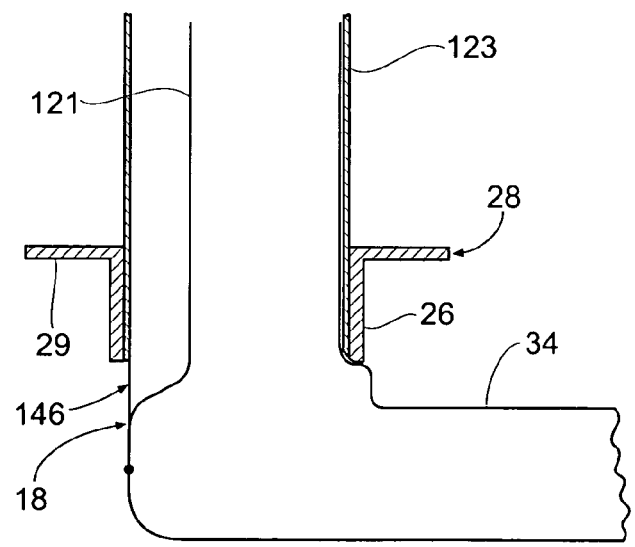
FIG. 10 is an enlarged cross-sectional view of another cannula capable, in use, of being inserted through the wall of a cavity, and having a bent distal region and a closure assembly that opens and closes fluid circulation within the cannula.
Figure 8:
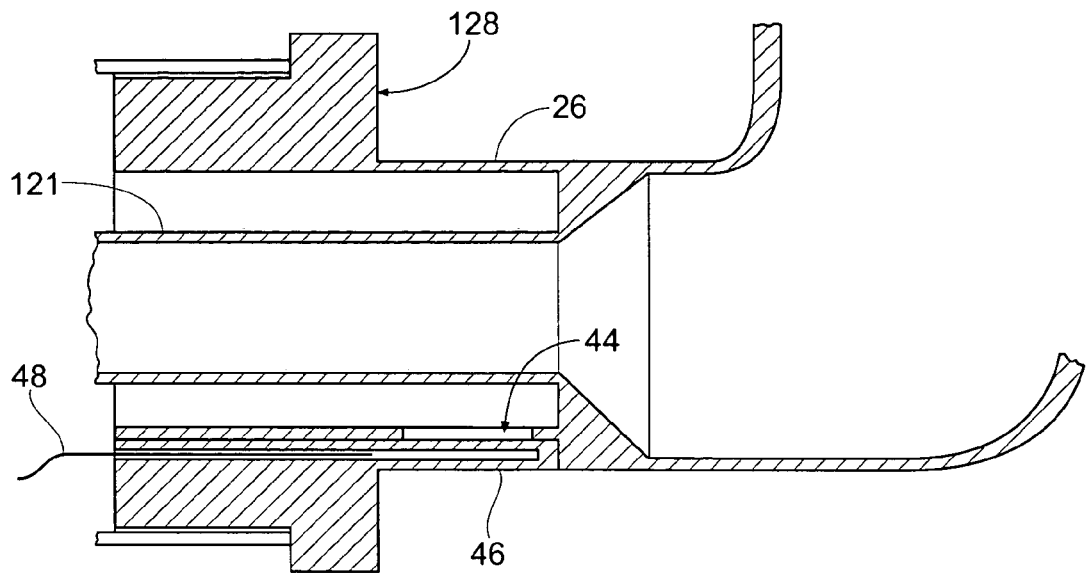
FIGS. 8 and 9 are enlarged cross-sectional views of another cannula capable, in use, of being inserted through the wall of a cavity, and having a bent distal region and a closure assembly that opens and closes fluid circulation within the cannula.
Figure 9:
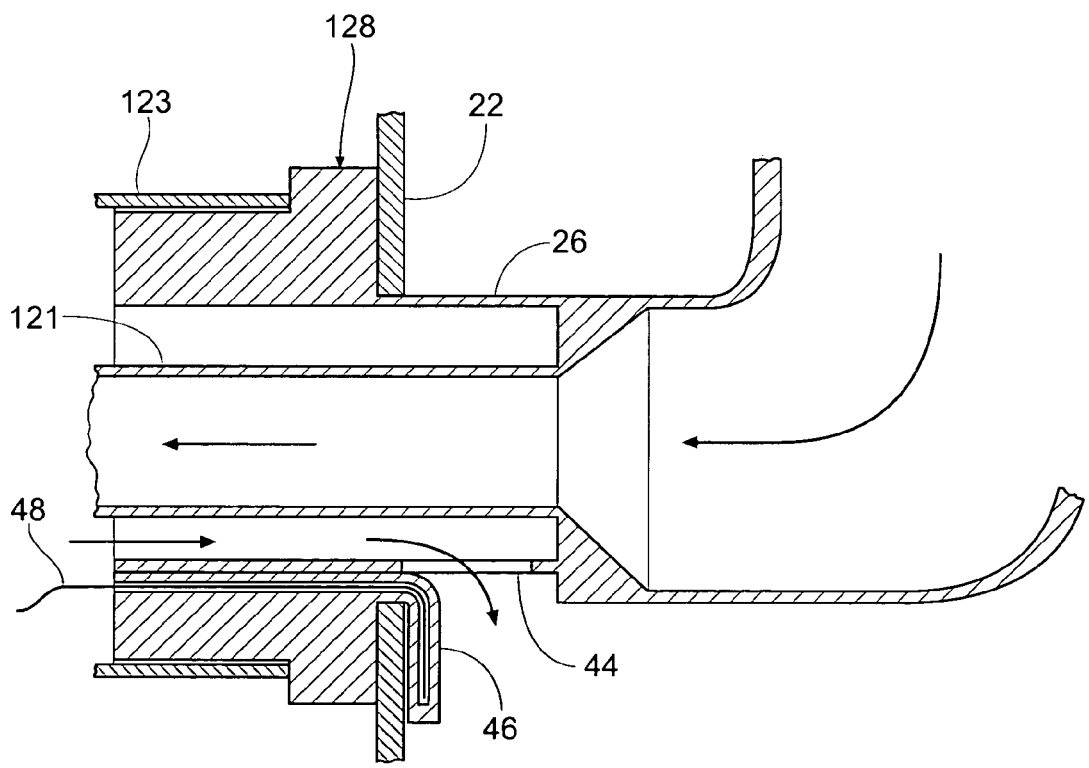

FIGS. 8 and 9 are enlarged cross-sectional views of a third embodiment of the present invention that provides the same benefit of easy insertion and withdrawal of a single outside diameter and concealed port as described above. The flange connector 128 has at least one but preferably three openings 44 (only 1 shown) through its wall at distal end 26. Flange connector 128 has a corresponding number of seal flaps 46 which initially cover corresponding openings 44 for insertion (and withdrawal) of the cannula system through the incision in the body cavity. An actuator 48 (e.g., NITINOL shape memory alloy wire) is located in a slot in the flange connector 128. After the cannula system is inserted into the body cavity 22, the actuator 48 is pushed into the slot in the seal flap 46 to open the outlet 44 and seal alone, the inner wall of the body cavity. FIG. 10 is an embodiment very similar to the third embodiment of FIGS. 8 and 9 except that the conduits are offset similar to FIGS. 6 and 7 and the flap 146 slides proximally to expose the outlet.

Figure 11:
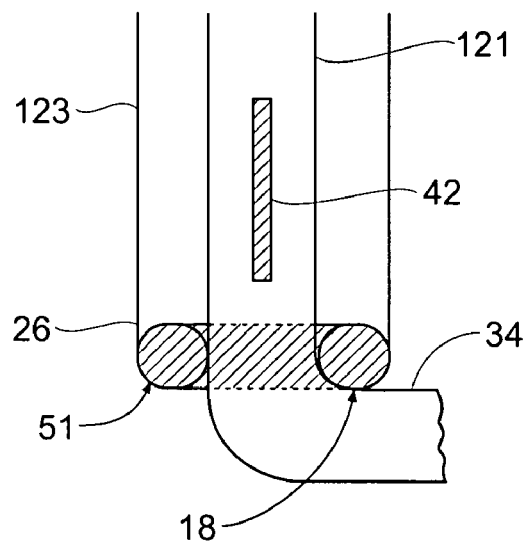
FIG. 11 is an enlarged cross-sectional view of another cannula capable, in use, of being inserted through the wall of a cavity, and having a bent distal region and a closure assembly that opens and closes fluid circulation within the cannula.
Figure 12:
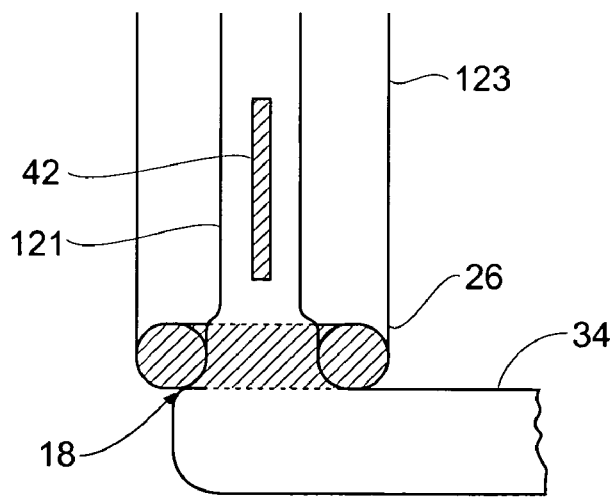
FIG. 12 is an enlarged cross-sectional view of another cannula capable, in use, of being inserted through the wall of a cavity, and having a bent distal region and a closure assembly that opens and closes fluid circulation within the cannula.

Two more embodiments that are similar are shown in FIGS. 11 and 12. The fifth embodiment shown in FIG. 11 has a balloon 51 located at the distal end 26 of the outer cannula 123 which when inflated as shown occludes the opening, to form the seal shown generally at 18 between the inner and outer conduit. When inflated for insertion, the balloon 51 provides a smooth rounded outer surface for inserting through an incision. The balloon can be attached to the outer cannula 123 or the inner cannula 121. In the sixth embodiment shown in FIG. 12, the outer diameter of the inner conduit 121 (which extends beyond the distal end 26 of the outer conduit 123) is shaped to provide a smooth transition with the inflated balloon 51

Figure 13:
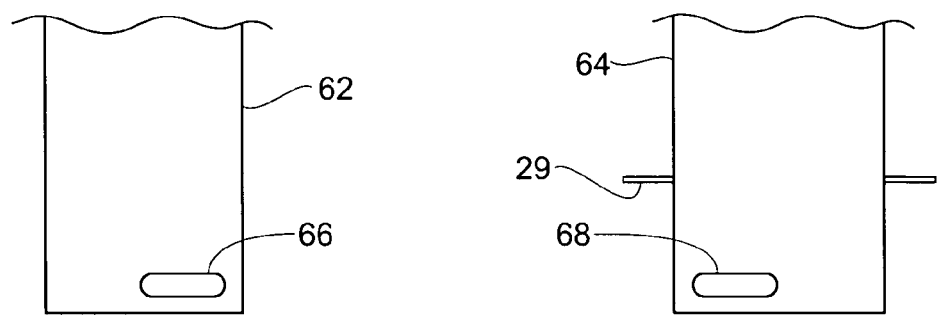
FIGS. 13 to 15 are enlarged cross-sectional views of another cannula capable, in use, of being inserted through the wall of a cavity, and having a bent distal region and a closure assembly that opens and closes fluid circulation within the cannula.
Figure 14:
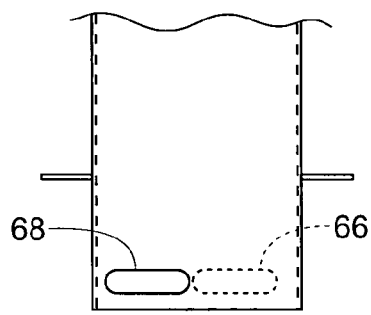
Figure 15:
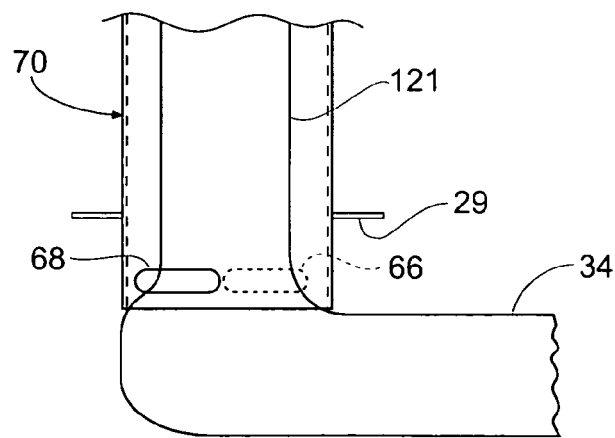

The seventh embodiment shown in FIGS. 13–15 has two outer cannulas 62 and 64. The outermost cannula 64 slides over the cannula 62 with the opening, 66 in cannula 62 initially being offset from opening 68 in cannula 64 as shown in FIGS. 14 and 15. The outermost cannula 64 and cannula 62 are slid over the inner cannula 121 until coming in contact with the outer diameter of the inner cannula as shown in FIG. 15 to form a seal therebetween. The cannula system 70 is inserted into a body cavity with the two openings 66 and 68 misaligned. The outermost cannula 64 is rotated with respect to the cannula 62 to align the openings 66 and 68 to allow fluid to flow therein or out therefrom.

In a preferred embodiment of the present invention, the longer inner cannula 121 is extended through the aortic valve (not shown) into the left ventricle (not shown) by way of the adapter portion 32 and flexible inlet conduit 34. Insertion of conduit 34 into the left ventricle may be accomplished with use of a guidewire. The length in which conduit 34 extends into the left ventricle depends on the beating or still heart bypass surgery procedures performed and on other factors known by those of ordinary skill in the art. The blood flow from the pulmonary vein (not shown) enters the left atrium (not shown) and is normally pumped through the left ventricle (not shown) into aorta 22. With the pump and cannula system of this invention, a portion or all of the blood from the left atrium enters pump 124 through the inlet conduit 34 and inner cannula 121 and is pumped through the annular space between outer cannula 123 and inner cannula 121 into the aorta 22 to assure the maintenance of adequate aortic blood flow during beating or still heart surgery. The pump and cannula system of the present invention is capable of maintaining a flow of five liters per minute, and more preferably, seven liters per minute. As will be recognized by one skilled in the aft, the above discussed cannulas and conduit will be made of appropriate flexible bio-compatible materials which have sufficient flexibility, radial stiffness and other strength properties 5 appropriate to the function intended in this invention. In most applications the cannulas and conduit utilized in this invention must have appropriate radial strength and stiffness to resist collapsing or kinking under the stresses and compressive loads imposed on them when inserted in the appropriate blood vessels during, beating or still heart bypass surgery. In some instances, soft and flexible materials such as silicones may be desirable and may need to be reinforced with wire or other material to provide the radial stiffness and resistance to collapsing necessary to be useful in the present invention.

The pump(s) of the systems of the present invention can be controlled in response to conventional parameters, such as oxygen level measured by conventional means, blood pressure measured by conventional means, or other parameters desired to assure proper patient support during and after surgery.

Another advantage of the system of the present invention is that the dual cannula in combination with the reverse flow miniature pump, such as disclosed in copending U.S. application Ser. No. 08/933,566, enables the installation of the pump essentially adjacent to the incision where the dual cannula is inserted into the aorta or other appropriate location. Thus, the priming volume of the pump and cannula system is minimized to less than about 1,000 preferably less than about 500 ml, and more preferably less than about 200 ml. In this context, "priming volume" refers to the volume of the pump and cannula which is external of the patient and does not include the volume of the portions of the cannula and inlet conduit which are inserted into the patient and thus are immersed in the blood flow. It Is especially preferred that the pump and cannula system priming, volume be very small, typically less than 30 ml, preferably less than 20 ml, and most preferably less than about 10 ml. In this regard, it is within the scope of the invention and definition of the outer cannula that its length be very short so as to appear as a plug at the incision Another advantage provided by the cannula system of this invention is that by having the capability of placing the small primarily volume pump adjacent to or very near the incision, the distance the blood must travel outside the body is minimized, the contact of the blood with tubing, pump components and other apparatus is minimized, and the pump can operate essentially at body temperature, thus eliminating the necessity of cooling or warming the blood, particularly because the blood is outside the body a very short distance and for a very short time. With this system the entire cannula system can be positioned near the chest cavity, within the chest cavity itself, near or adjacent to the heart to obtain the minimum possible pumped blood flow path. Other advantages include the fact that with the cannula system miniaturized and configured to be contained in the chest cavity, this system eliminates the disadvantages of having numerous tubes, cables, etc., from the patient's chest cavity to external equipment. In the preferred embodiment of the present invention, the only lines extending from this system to external equipment is a single cable from the pump to the external power supply for providing power to the pump. This single cable can contain electrical connection for supplying electrical power to the pump motor near the heart or can be a flexible drive cable to transmiting power from a remote motor to the pump in or near the heart. Thus, the cannula system of this invention provides the surgeon better surgical access to the heart and visibility of the heart by eliminating the CPB tubing and other associated cables and pumps which are conventionally used in bypass surgery.

Another advantage of the present invention is that the fluid in the outer cannula acts as a safety feature preventing air from being drawn into the body cavity. If the inner cannula was not drawing fluid, rather than pulling air in around the distal end 26 of the flange adapter, the system would draw the fluid from the annular space 24 into the body cavity to prevent embolism. As will be apparent to one skilled in the art, the above description of the cannula system and reverse flow pump having a minimum priming volume constitute preferred embodiments of the present invention, but other pump and cannula configurations and designs may be employed in the cannula systems of the present invention. For example, an inner cannula may be inserted to draw fluid into an in-line pump which can then return the fluid through a looped conduit back to the outer cannula. Thus, various conventional pumps can be used in accordance with the cannula systems of this invention even those of large priming volume.

Another embodiment of the present invention provides a cannula assembly which has been specifically adapted for insertion within the patient's heart. The cannula assembly allows, for example, the user to insert a first cannula into the right atrium and advance the distal tip of the first cannula into the right ventricle. The distal tip of the first cannula is curved, to guide a second cannula through the first cannula and advance the second cannula into the pulmonary artery. After placing the second cannula through first cannula and into the pulmonary artery, a blood pump can be attached to the proximal end of the cannula assembly. Thereafter the pump and cannula assembly may be utilized to provide support to the right side of the beating heart.

The cannula assembly comprises a substantially tubular, semi-flexible material adapted for fluid transport while inserted in a patient's body, and is provided with a curved distal tip or guide tube. The cannula assembly may further be adapted to support a stiffening wire to aid the operator in its insertion through the patient's body, and/or a light source to provide a visual reference during the insertion procedure. Further the cannula assembly may contain lumens disposed within the wall of the cannula, these lumens may be utilized to inflate or deflate balloons disposed about the outer surface of the cannula, or alternatively at least one pressure transducer may be disposed sufficiently closed to the main lumen of the cannula for pressure measurements. Still further the cannula assembly may contain more than one pressure transducer disposed adjacent to the inner wall, thereby allowing the user to determine a flow rate within the cannula.

An exemplary arrangement of such a cannula assembly 210 is shown in FIGS. 16 to 19. The cannula assembly 210 comprises a substantially cylindrical structure having main tube 220 with wall 218 defining a main lumen 211, an inflow port 230, and a formed curved portion 240. Wall 218 can be formed of materials ranging from rigid too flexible, and in the preferred embodiment comprises a semi-rigid transparent material such as polyurethane, polyvinyl chloride (PVC) or other material. Lumens other than main lumen 211 may also be provided, as described below.

To lend structural support, spiraling wire (not shown) may be provided for reinforcement, which is generally molded into the wall 218 of cannula assembly 210. The wire further facilitates handling of cannula assembly 210 and reduces the possibility of cannula assembly 210 collapsing or being pinched shut and thus closing off the flow of fluid to or from the patient or preventing the user from passing a inner cannula through lumen 211 of cannula assembly 210. Other ways of reinforcing the tubular body of cannula assembly 210 are known in the art and will adapt equally well to the present invention. In addition, no reinforcement may be needed if the cannula material is sufficiently rigid or if sufficient fluid pressure is present within the cannula. The pitch, in which the wire is wound within cannula wall 218 can be altered to vary the stiffness of the curved portion 240 of cannula assembly 210. By altering the winding pitch during the manufacturing process the stiffness of curved portion 240 can be altered. Thus the curved portion 240 may be formed so that it is sufficiently stiff to provide the user with the ability to align distal tip 241 with the patient's pulmonary artery so that a second cannula may be passed through lumen 211. Still, the curved portion 240 must be sufficiently flexible such that when the heart is rotated curved portion 240 will deflect or rotate with the heart. Alternatively, the curved portion 240 may not be reinforced with wire.

Figures 16, 17, 18:
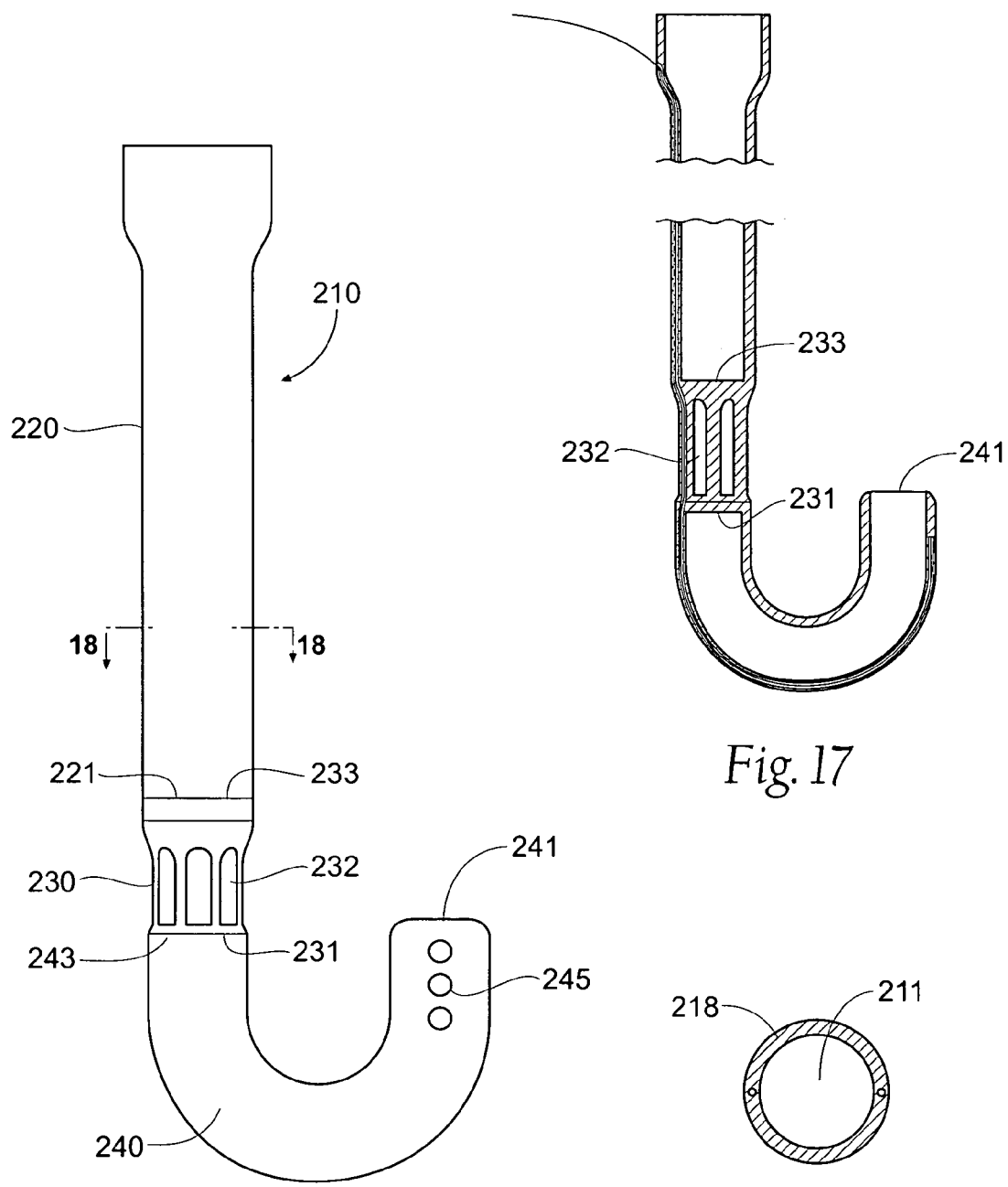
FIG. 16 is a side view of a cannula system capable, in use, of being inserted through the wall of a cavity, and having a bent distal region that aids insertion of a cannula into a heart chamber.
FIG. 17 is a sectional view of the cannula system shown in FIG. 16.
FIG. 18 is a cross sectional view taken about line 18—18 of FIG. 1.

As illustrated in FIGS. 16 to 22, cannula assembly 210 is constructed by combining main body 220, the inflow port 230, and the curved portion 240. Inflow port 230 may be molded of polyurethane, or polyvinyl chloride, most preferably inflow port 230 is constructed of urethane. As illustrated in FIGS. 16 and 17, inflow port 230 contains openings 232, distal end 231, and proximal end 233. Proximal end 233 of inflow port 230, is further adapted to receive distal end 221 of tube 220 of cannula assembly 220. Distal end 231 of inflow port 230 is adapted to receive proximal end 243 of curved tube 240.

The curved tube 240 may be constructed of materials ranging from rigid too flexible, and in the preferred embodiment comprises a semi-rigid transparent material such as polyurethane, polyvinyl chloride or other material. Further, the curved tube 240 may contain apertures 245 disposed adjacent to tip 241 and along the length of the curve. Further tip 241 is formed so that it is sufficiently smooth such that tissue will not be damaged if contacted. Tip 241 is further adapted to provide a seal about cannula 260 when cannula 260 is disposed through tip 241 (see FIG. 23). Curved portion 240 and tip 241 may be constructed of different materials which are then bonded together through the use of solvents or heat. Curved portion 240 may be constructed having varied wall thickness. Further curved portion 240 may be constructed of a material having a different durometer than distal tip 241.

Figures 20, 21:
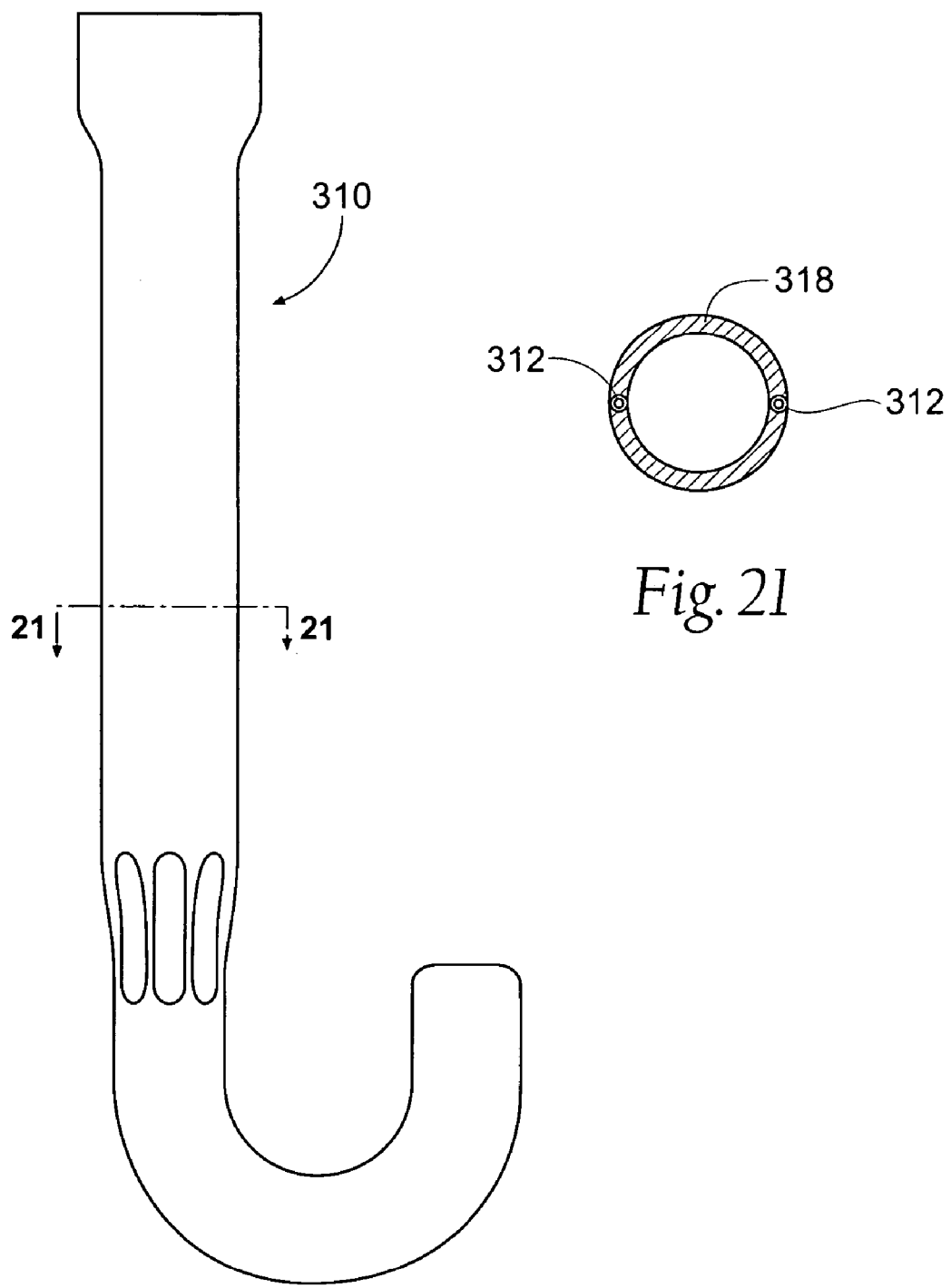
FIG. 20 is a side view of another cannula system capable, in use, of being inserted through the wall of a cavity, and having a bent distal region that aids insertion of a cannula into a heart chamber.
FIG. 21 is a cross sectional view about line 21—21 of FIG. 20.

As illustrated in FIGS. 16 and 20, distal tip 241 may be constructed of a similar material as the curved portion 240 though of a different durometer. Tip 241 may be constructed of a more resilient material than curved portion 240 such that if tip 241 contacts the patient's tissue it will not abrade the patient's tissue thereby causing further damage.

Figure 19:
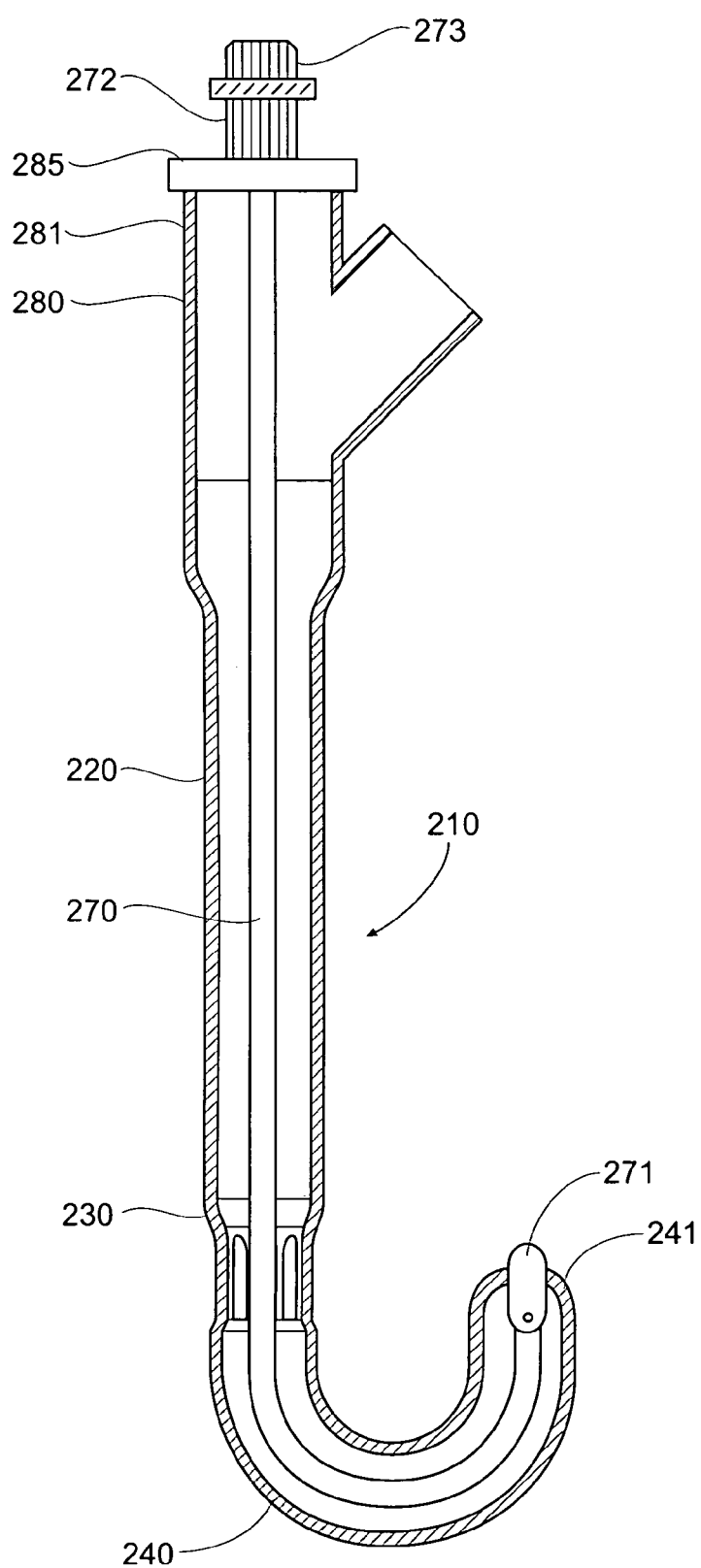
FIG. 19 is a side sectional view of the cannula system shown in FIG. 1 after insertion of an obturator.

As illustrated in FIG. 19, prior to insertion into the patient's body, cannula 210 further contains a flexible obturator 270 disposed within main lumen 211. Distal tip 271 of obturator 270 is further adapted to seal inflow port 241 during insertion and to provide a smooth transition between distal tip 271 of obturator and distal tip 241 of cannula assembly 210. Proximal end 272 of obturator 270 further contains handle 273. During assembly handle 273 of obturator 270 is placed such that when obturator 270 is fully inserted within cannula assembly 210, distal tip 271 seals distal tip 241 of cannula assembly 210. Placement of handle 273 further ensures that distal tip 271 of obturator 270 does not protrude substantially beyond distal tip 241 of cannula assembly 210.

As illustrated in FIGS. 20 and 21, cannula 310 may be constructed as a unitary construction having a smooth inner and outer surface. It is also constructed of a soft, resilient material, such as urethane though preferably constructed of polyvinyl chloride (PVC). Cannula 310 may further include spiral wire reinforcement (not shown) disposed within the cannula wall, further cannula 310 may contain malleable material 312 disposed within wall 318 of cannula 310. Malleable material 312 allows the cannula to be shaped into a desired form before inserting cannula 310 into the patient. Cannula 310 is manufactured by a dip-molding process utilizing a mandrel as an inner mold.

Figure 22:
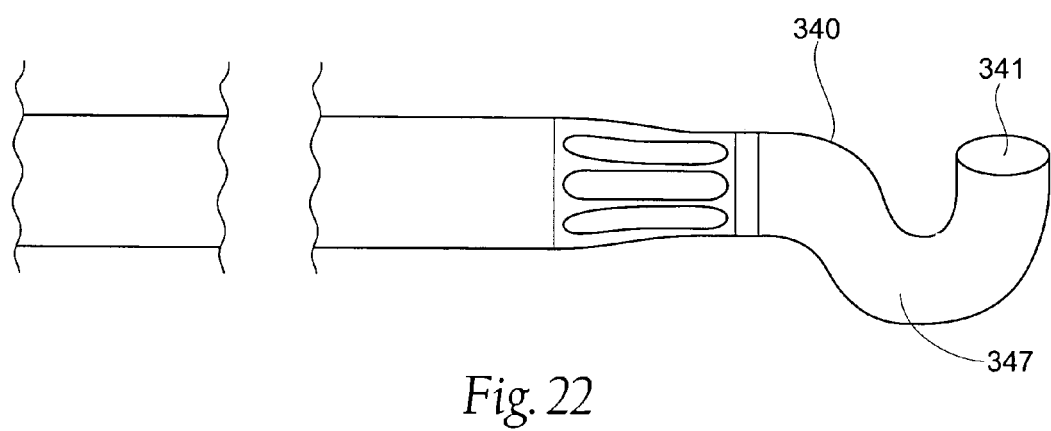
FIG. 22 is a side view of another cannula system capable, in use, of being inserted through the wall of a cavity, and having a distal region having multiple bends that aids insertion of a cannula into a heart chamber.

Alternatively as illustrated in FIG. 22, cannula assembly 300 may contain more than one curved portion 340, 347 within one or more planes. Therefore, cannula assembly 300 is bent in at least two directions. Curved portion 340, 347 aids the user in aligning distal tip 341 with the patient's pulmonary artery.

Figure 23:
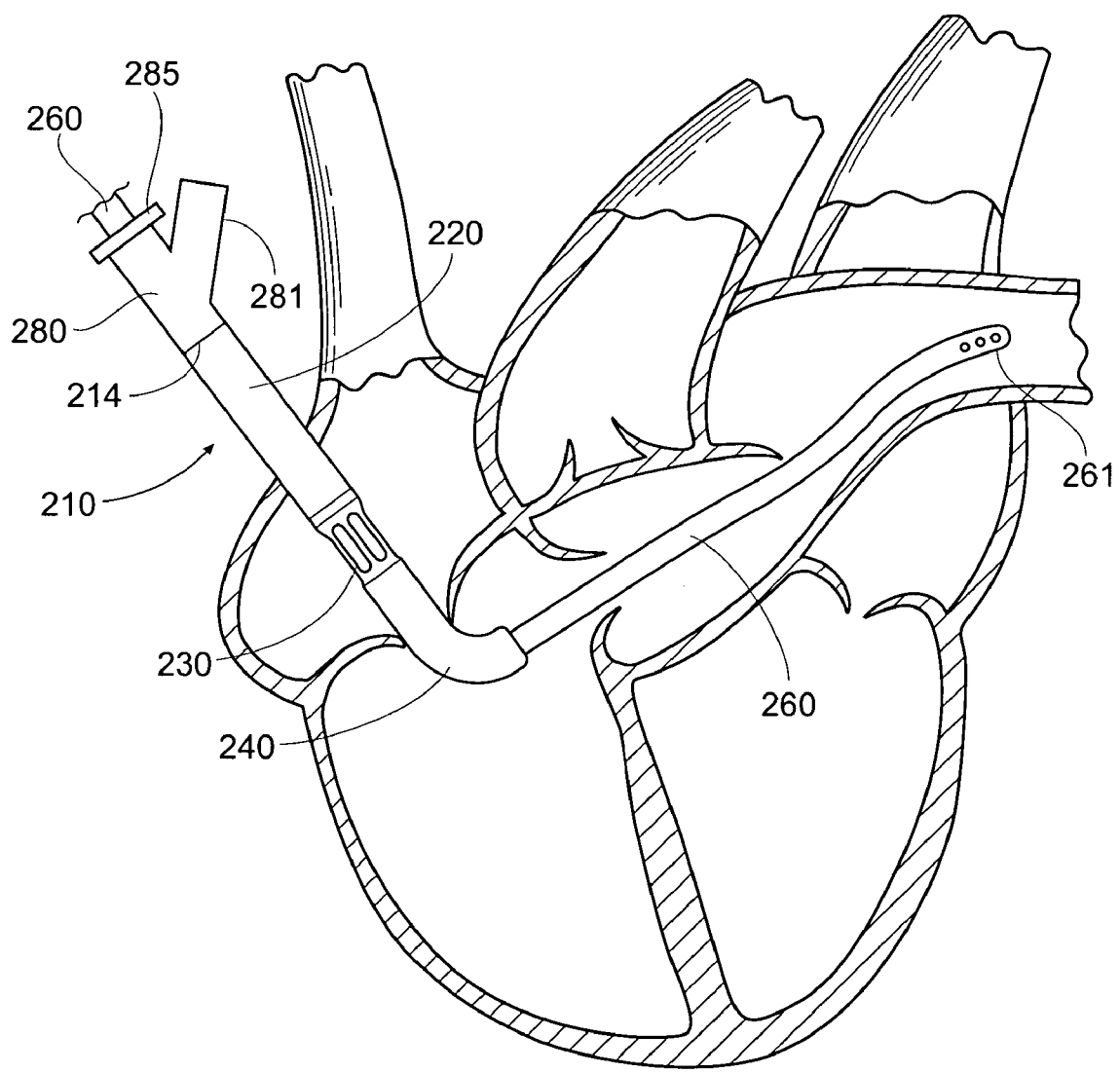
FIG. 23 is a view of a cannula system having a bent distal region inserted into the right heart.

In use, as illustrated in FIG. 23, cannula assembly 210 is inserted within the patient's body through the right atrium. Distal tip 241 of cannula assembly 210 is disposed within the patient's right ventricle by advancing cannula assembly 210 through the right atrium and tricuspid valve. After cannula assembly 210 is placed within the patient's right ventricle, inner cannula 260 is inserted proximally through main lumen 211 of cannula assembly 210. Inner cannula 260 is advanced through lumen 211 of cannula assembly 210 until distal tip 261 of inner cannula 260 is placed within the patient's pulmonary artery. Curved portion 240 of cannula assembly 210 aids in placing distal tip 261 of inner cannula 260 into the patient's pulmonary artery by providing the user with a means for advancing inner cannula 260 without the need for supplemental guiding means, such as a guidewire or balloon catheter. After placing inner cannula 260 within the patient's pulmonary artery, cannula 260 is clamped proximal to the y-connector 280, thereby restricting cannula 260 from moving independent of cannula assembly 210.

As illustrated in FIGS. 19 and 20, cannula assembly 210 may further contain y-connector 280 disposed about proximal end 214 of cannula assembly 210. Y-connector 280 further contains hemostasis valve 285 disposed about proximal end 281 of y-connector 280. Hemostasis valve 285 seals around inner cannula 260, thereby allowing the inner cannula to move relative to the outer cannula and further reducing the possibility of blood leakage or emboli forming within the patient's blood stream. Hemostasis valve 285 is described in U.S. patent application Ser. No. 09/163,102 and U.S. patent application Ser. No. 09/163,103.

Figure 24:
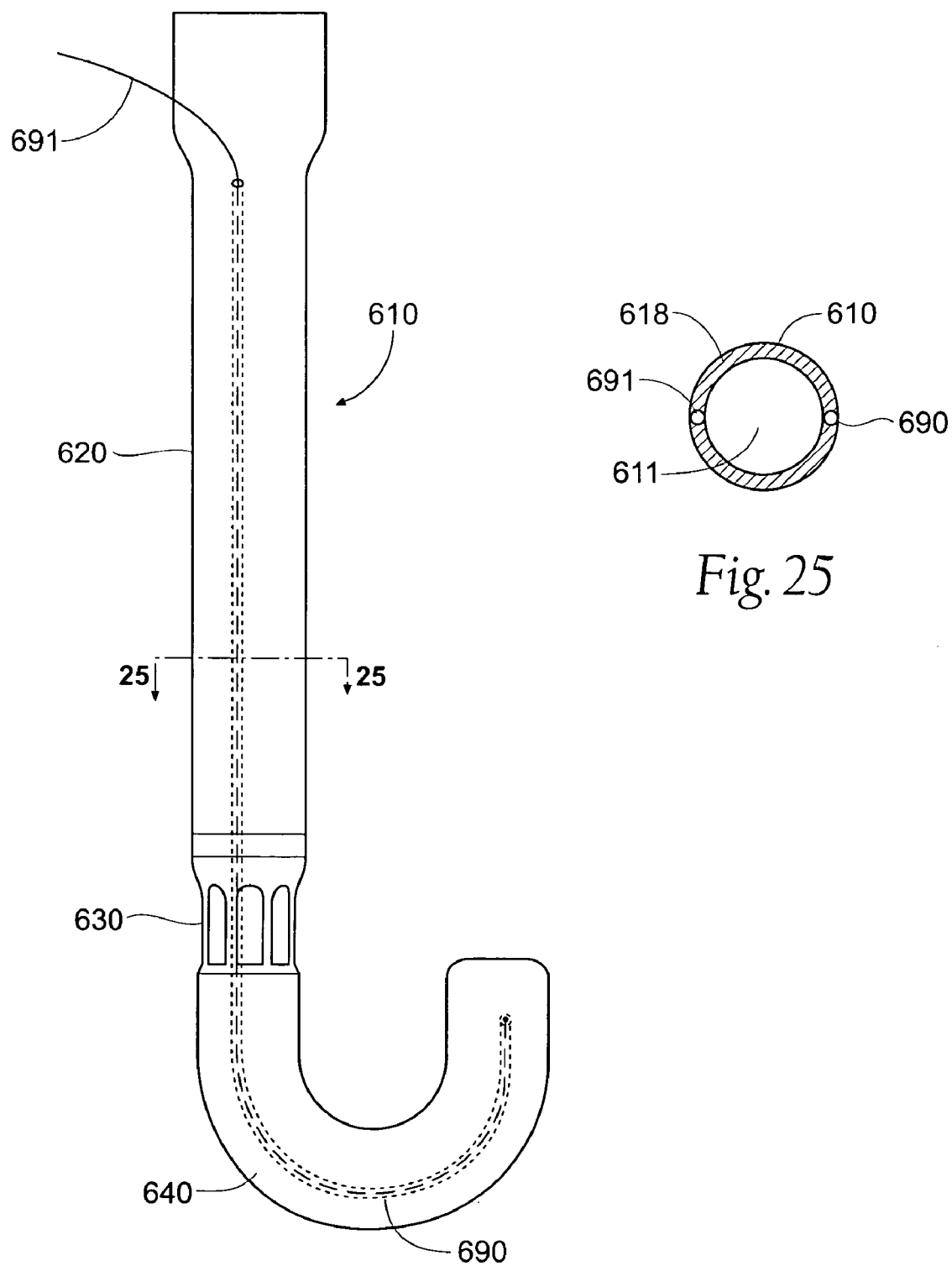
FIG. 24 is a side view of another cannula system capable, in use, of being inserted through the wall of a cavity, and having a bent distal region that aids insertion of a cannula into a heart chamber.
Figure 25:
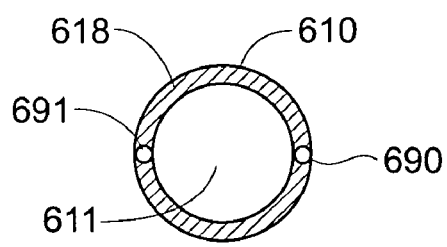
FIG. 25 is a cross sectional view about line 25—25 of FIG. 9.

A further embodiment of the invention is illustrated in FIGS. 24 AND 25. Cannula assembly 610 consists of a main tube 620, an inflow port 630, and a curved portion 640. Further, cannula assembly 610 contains lumen 690 disposed axially through wall 618 of main tube 620, inflow port 630, and pre-curved portion 640. Lumen 690 may contain stylet 691 which allows the user to adjust the curvature of curved tip 640 of cannula assembly 610. Initially stylet 691 is inserted through lumen 690 in cannula wall 618. After placing cannula assembly 610 within the patient's heart, stylet 691 may be removed thereby enabling curved portion 640 of cannula assembly 610 to become more flexible. Alternatively, curved tip 640 may further contain steering wire fixedly attached within lumen 690 of cannula assembly 610 adjacent to distal tip 641. By manipulating proximal end of steering wire, the operator may adjust the curvature of the distal tip 641 of cannula assembly 610.

As illustrated in FIGS. 26 AND 27, distal tip 741 may further contain wire 791 having resistive joint connections 795 forming a continuous wire. Lumen 790 disposed axially through cannula assembly 710, having electrical wire 796 in communication with wire 791 disposed within distal tip 741 of cannula assembly 710. Proximal end of electrical wire 796 is connected to an adjustable current source. As illustrated in FIG. 27, distal tip of cannula assembly 710 can be selectively curved by passing an electrical signal through electrical wire 796. The electrical signal is passed to wire 791, where selective resistive joints 795 will sever, allowing the distal tip 741 to assume a pre-determined curved shape. Prior to assembly, distal tip 741 of cannula assembly 710 is formed having a curved portion 740. Tip 741 further contains lumen 790 though which wire 791 may be disposed, thereby straightening tip 741 for insertion into the patient. After inserting cannula assembly 710 into the patient's right ventricle, a current means is activated thereby severing a selective joint 795, thus allowing distal tip 741 to curve into a pre-determined shape.

An alternative method of selectively bending distal tip, would be to use a memory shape alloy metal such as Nitinol which reacts to changes in temperatures. Therefore, curved portion 740 of cannula assembly 710 may be formed having an initial curvature. Before insertion into a patient the cannula is either heated or chilled, thereby activating the Nitinol wire which straightens the cannula for insertion into the patient. After insertion into the patient, the cannula warms to the temperature of the blood flowing therethrough, thus causing the tip of the cannula to return back to its pre-curved state.

Alternatively, curved portion 740 of cannula assembly 710 containing Nitinol wire may be initially formed with a curvature adjacent to distal tip 741. Whereby after inserting cannula assembly 710 into the patient's heart, cannula assembly 710 is warmed to body temperature thereby activating the Nitinol wire which allows curved portion 740 to become flexible. Thus, if the heart is rotated curved portion 740 will not resist the rotation of the heart.

It will now be apparent to those skilled in the art that various modifications, variations, substitutions, and equivalents exist for various elements of the invention but which do not materially depart from the spirit and scope of the invention. Accordingly, it is expressly intended that all such modifications, variations, substitutions and equivalents which fall within the spirit and scope of the invention as defined by the appended claims be embraced thereby.

We claim:

1. A method of providing cardiac support comprising
providing a first cannula body having a main lumen and a proximal opening and distal opening communicating with the main lumen, the first cannula body including a preformed bend near the distal opening,
providing a second cannula body having an interior lumen and a distal opening communicating with the interior lumen,
inserting the first cannula body through a first valve that leads into a heart chamber such that the distal opening of the first cannula body is located within the heart chamber,
orienting the preformed bend toward a second valve that leads out of the heart chamber to a vascular region spaced from the heart chamber,
inserting the second cannula body into the main lumen through the proximal opening,
advancing the second cannula body through the preformed bend to direct the second cannula body beyond the distal opening of the first cannula body, into the heart chamber and through the second valve, such that the distal opening of the second cannula body resides within the vascular region, and
bypassing the heart chamber by drawing blood into the main lumen of the first cannula body through an inlet upstream of the first valve, conveying the blood from the main lumen of the first cannula body into the interior lumen of the second cannula body, and discharging the blood into the vascular region through the distal opening of the second cannula body downstream of the second valve.

2. A method according to claim 1
wherein the heart chamber is a right ventricle,
wherein the first valve is a tricuspid valve, and
wherein the second valve is a pulmonary valve.

3. A method according to claim 1
wherein the heart chamber is a left ventricle,
wherein the first valve is an aortic valve, and
wherein the second valve is a mitral valve.

* * * * *